US 6,709,448 B2

(12) United States Patent
Walker et al.

(10) Patent No.: US 6,709,448 B2
(45) Date of Patent: Mar. 23, 2004

(54) OPEN CORE HEAT EXCHANGE CATHETER, SYSTEM AND METHOD

(75) Inventors: Blair D. Walker, Mission Viejo, CA (US); Wayne A. Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/120,587

(22) Filed: Apr. 11, 2002

(65) Prior Publication Data

US 2002/0151942 A1 Oct. 17, 2002

Related U.S. Application Data

(60) Provisional application No. 60/283,349, filed on Apr. 13, 2001.

(51) Int. Cl.⁷ .................................................. A61F 7/00
(52) U.S. Cl. ........................ 607/105; 607/106; 604/113
(58) Field of Search ........................... 607/96, 104–106, 607/113; 604/113

(56) References Cited

U.S. PATENT DOCUMENTS

| | | |
|---|---|---|
| 3,425,419 A | 2/1969 | Dato |
| 4,038,519 A | 7/1977 | Foucras |
| 4,941,475 A | 7/1990 | Williams et al. |
| 4,945,912 A | 8/1990 | Langberg |
| 5,151,100 A | 9/1992 | Abele et al. |
| 5,279,598 A | 1/1994 | Sheaff |
| 5,370,616 A | 12/1994 | Keith et al. |
| 5,383,856 A | 1/1995 | Bersin |
| 5,486,208 A | 1/1996 | Ginsburg |
| 5,498,261 A | 3/1996 | Strul |
| 5,542,928 A | 8/1996 | Evans et al. |
| 5,549,552 A | 8/1996 | Peters et al. |
| 5,797,948 A | 8/1998 | Dunham |
| 5,807,395 A | 9/1998 | Mulier et al. |
| 5,899,899 A | 5/1999 | Arless et al. |
| 5,919,187 A | 7/1999 | Guglielmi et al. |
| 5,957,963 A | 9/1999 | Dobak, III |
| 5,964,744 A * | 10/1999 | Balbierz et al. ............. 604/530 |
| 6,011,995 A | 1/2000 | Guglielmi et al. |
| 6,051,019 A | 4/2000 | Dobak, III |
| 6,096,068 A | 8/2000 | Dobak, III et al. |
| 6,126,684 A | 10/2000 | Gobin et al. |
| 6,149,677 A | 11/2000 | Dobak, III |
| 6,190,356 B1 | 2/2001 | Bersin |
| 6,224,624 B1 | 5/2001 | Lasheras et al. |
| 6,231,594 B1 | 5/2001 | Dae |
| 6,241,722 B1 | 6/2001 | Dobak et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,290,685 B1 | 9/2001 | Insley et al. |
| 6,312,452 B1 | 11/2001 | Dobak, III et al. |
| 6,338,727 B1 | 1/2002 | Noda et al. |
| 6,533,804 B2 * | 3/2003 | Dobak et al. ............... 607/105 |

* cited by examiner

Primary Examiner—Roy D. Gibson
(74) Attorney, Agent, or Firm—John L. Rogitz

(57) ABSTRACT

A heat exchange catheter having an open core includes a catheter body for use in the central vasculature of a patient. The catheter body having a balloon with at least one heat exchange lumen for exchanging heat with flowing blood. The balloon inflates from a collapsed configuration to an inflated configuration. In the inflated configuration the balloon facilitates the flow of heat exchange fluid through the heat exchange lumen, which wraps in a helical pattern to define the open core and to enable blood to flow through the open core during use of the catheter. The open core defines an inside and an outside, the heat exchange lumen has non-contiguous helical winds to allow flowing blood to mix between the inside of the open core and the outside of the open core.

17 Claims, 4 Drawing Sheets

OPEN CORE HEAT EXCHANGE CATHETER, SYSTEM AND METHOD

This application claims the benefit of Application No. 60/283,349, filed Apr. 13, 2001.

FIELD

This invention relates to heat exchange catheters, and particularly to catheters that exchange heat with the blood stream of a patient.

BACKGROUND

Heat exchange catheters are used in many instances for a variety of reasons. Some surgeries, for example, are better performed when the patient cools to a hypothermic state. In other instances, a patient may suffer from accidental hypothermia and may need to be warmed to a normothermic temperature e.g. 98.6° F. Many heat exchange catheters include the capability of infusing fluids such as nutrition, medicine and contrast agents into the blood.

Post surgical patients risk infection and fever. A fever can be controlled through the use of a heat exchange system having an intravascular heat exchange catheter. One such system is disclosed in commonly assigned U.S. Pat. No. 6,146,411, issued Nov. 14, 2000 and incorporated herein by reference. This U.S. patent teaches an exemplary system used to regulate patient temperature.

The principals of heat exchange applicable to any flowing medium (including blood) dictates the amount of heat transfer. In blood, the heat transferred depends on many things including the volumetric flow rate of the blood, the geometry of the heat exchanger and the temperature difference between the heat exchanger and the blood.

Blood has a maximum desirable heating limit. Beyond about 41° C., blood coagulates. This limits the maximum operating temperature of known intravasculature catheters. Because the operating temperature of an intravascular catheter is limited, the catheter geometry takes on an increased importance to effectuate overall heat transfer.

Commonly assigned U.S. Pat. No. 6,126,684 issued Oct. 2, 2000 is incorporated herein by reference. This teaches a heat exchange catheter having smooth tubular balloons in serial alignment to exchange heat with the blood stream of a patient. The balloons each have an exterior surface that facilitates heat exchange with flowing blood.

U.S. Pat. No. 6,096,068 teaches a heat exchange catheter having a contoured outer surface and a heat exchange core. The contoured outer surface increases heat exchange surface area as compared to smooth tubular balloons. The contoured outer surface increases heat exchange fluid turbulence and flowing blood turbulence to improve heat transfer. These effects improve the heat transfer capability of the catheter.

U.S. Pat. No. 5,657,963, particularly the description of FIG. 6, teaches a catheter having heat exchange tubes having a nominal double helix configuration. The tubes themselves are formed from nitinol, a shape memory alloy. Initially the tubes are relatively straight at room temperature and insert into the vasculature in this straight configuration. Once inserted, commencement of refrigerant flow through the nitinol tubes causes the tubes to spiral, and thereby achieve more acute double helix configuration.

One difficulty with using alloy heat exchange tubes is that the flexibility and the tubes may be insufficient to effectuate safe insertion of the catheter into the vasculature of a patient. Further, while the helix may change shape, the nominal tube diameters may not change significantly. An unnecessarily large entry hole may be cut into one of the patients' primary blood vessels to facilitate insertion of the catheter tube into the vasculature.

What is desired is a heat exchange catheter having a geometry that is optimally designed for transferring heat to flowing blood, and which safely inserts into a patient.

SUMMARY

A vascular heat exchange catheter has an open core that allows blood to flow and which optimized heat transfer. The catheter has a catheter body with a balloon. The balloon has at least one heat exchange lumen for exchanging heat with flowing blood.

The balloon inflates from a collapsed configuration to an inflated configuration. In the inflated configuration, the balloon facilitates the flow of heat exchange fluid through the heat exchange lumen, the heat exchange lumen wraps in a helical pattern to define the open core and to enable blood to flow through the open core during use of the catheter.

According to one aspect of the invention, the open core defines an inside and an outside and the heat exchange lumen has contiguous helical winds to isolate the inside from the outside.

According to an alternate aspect of the invention, the open core defines an inside and an outside and the heat exchange lumen has non-contiguous helical winds. The non-contiguous helical winds facilitate movement of flowing blood between the inside of the open core and the outside the open core.

A heat exchange fluid source communicates with the heat exchange lumen. The heat exchange fluid source is pressure regulated for selectively inflating and collapsing the heat exchange lumen.

The catheter body includes an insertion rod for inserting the balloon into a patient and shaping the balloon. Preferably, the rod attaches to a distal end of the balloon. The rod is fabricated from a shape memory material that biases the balloon into the helical shape under desired conditions. The rod cooperates with the heat exchange fluid to shape the balloon into the inflated configuration.

DETAILED DESCRIPTION

Figure 1:
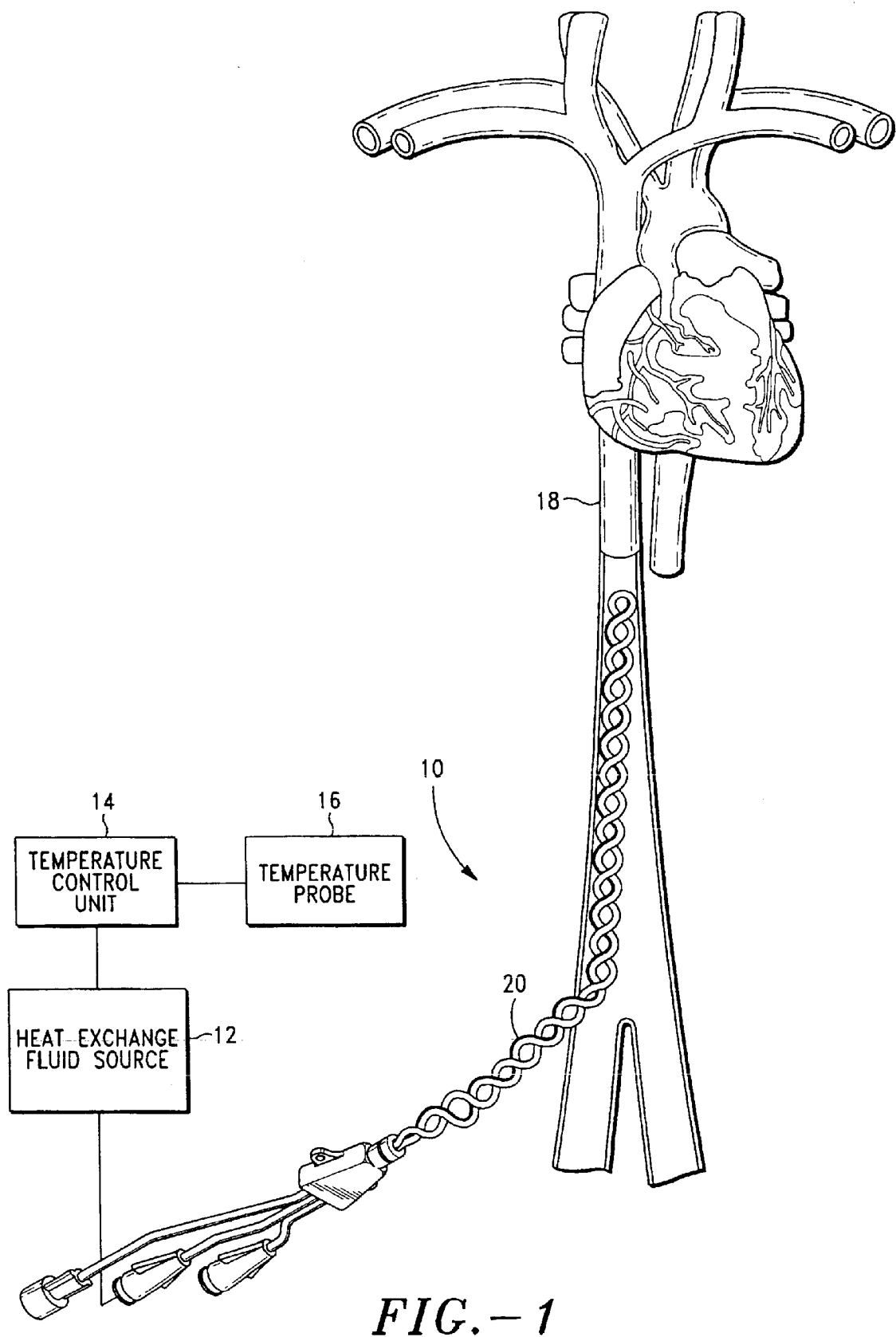
FIG. 1 shows a system in accordance with the present invention.

FIG. 1 shows a heat exchange catheter system having a heat exchange catheter 10, a heat exchange fluid source 12 and a temperature control unit 14 with a temperature probe 16. The catheter 10 inserts into the central vasculature 18 of a patient.

The temperature control unit 14 regulates heat exchange fluid source 12 temperature in response to the temperature probe 16. The heat exchange fluid source 12 circulates temperature-regulated heat exchange fluid through a closed loop via the catheter 10 to achieve patient warming, cooling, or temperature maintenance. An exemplary temperature control system is disclosed in U.S. Pat. No. 6,146,411, issued Nov. 14, 2000, the disclosure of which is incorporated herein by reference.

The catheter 10 has a helical balloon 20 to circulate the heat exchange fluid through the catheter 10. The heat exchange fluid source 12 is pressure regulated for selectively inflating and collapsing the balloon 20.

Figure 2:
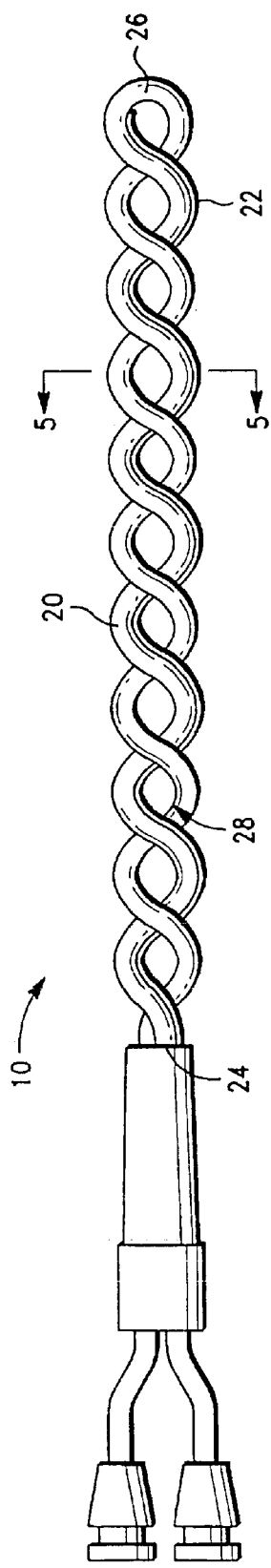
FIG. 2 shows a catheter having an open core and non-contiguous helical winds.

FIG. 2 shows the balloon 20 in an inflated configuration. In the inflated configuration, the balloon 20 optimizes heat exchange with flowing blood. The balloon 20, preferably inflates in response to the introduction of heat exchange fluid into the balloon 20. The balloon 20 collapses upon withdrawal of the heat exchange fluid.

The balloon 20 has a proximal end 24 and a distal end 26. According to one aspect of the invention, the balloon 20 has a rod 22 that extends in a helical pattern along the balloon 20 from the proximal end 24 to near the distal end 26. The rod 22 cooperates with the introduction and withdrawal of heat exchange fluid to assist the inflation and collapse of the balloon 20. The rod 22 improves pushability of the catheter 10 when the catheter inserts into the patient 10.

The balloon 20 has non-contiguous helical winds that form interstices 28 between each wind. The interstices 28 allow blood flowing within the core 32 (FIG. 5) of the catheter 10 to mix with blood on the outside of the catheter 10.

Figure 3:
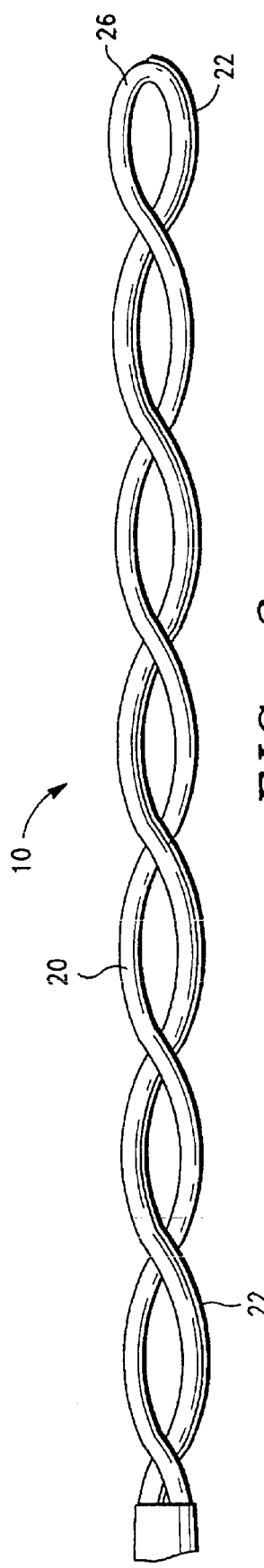
FIG. 3 shows a catheter having an adjustable length.

FIG. 3 shows an embodiment of the catheter 10 with the balloon 20 in the collapsed configuration. The rod 22 attaches to the distal end 26 and lengthens the balloon 20 to cause the catheter body to narrow. Using the rod 22 to lengthen and narrow the catheter body facilitates insertion of the balloon 20 into a patient.

Figure 4:
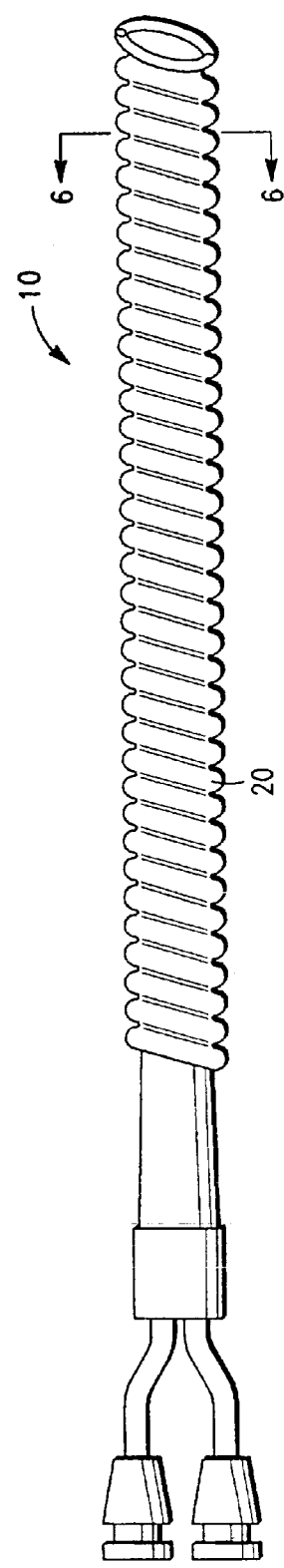
FIG. 4 shows a catheter having contiguous helical winds.

FIG. 4 shows an embodiment of the catheter 10 having a balloon 20 with contiguous helical winds. The contiguous helical winds prevent mixing of blood flowing outside of the catheter 10 with blood flowing inside of the catheter.

Figure 5:
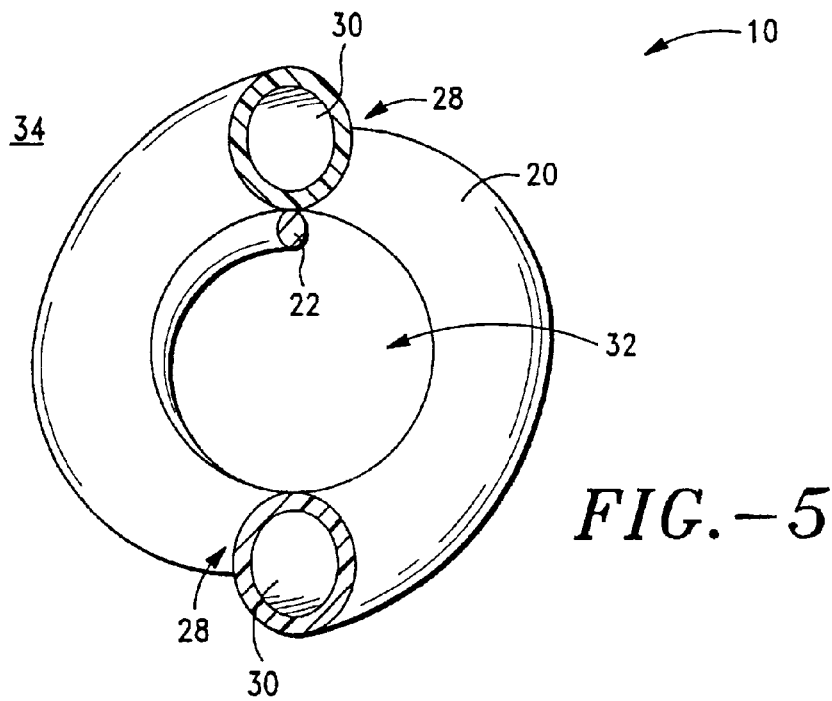
FIG. 5 shows a partial cross sectional end view of the catheter of FIG. 2 as seen along the line 5—5.

FIG. 5 shows a section of the catheter 10 including the balloon 20 of FIG. 2. The balloon 20, in the inflated configuration, forms a heat exchange lumen 30. The heat exchange lumen 30 facilitates the circulation of heat exchange fluid within the balloon 20.

The balloon 20, and the heat exchange lumen 30, wrap in a helical configuration to define an open core 32. The open core 32 facilitates circulation of blood through the catheter 10.

Ideally, but not necessarily, the catheter 10 is centrally positioned within a blood vessel during use so that blood flows both along the outside 34 of the catheter 10 and through the open core 32.

The helical configuration includes non-contiguous helical winds that define and includes helical interstices 28 (see also FIG. 2) between the helical winds of the balloon 20. The interstices 28 facilitate mixing of the blood flowing between the open core 32 and the outside 34 of the catheter 10. This mixing assures a generally uniform temperature gradient between the open core 32 and the outside 34 of the catheter 10 and optimizes heat transfer between the catheter 10 and flowing blood. The open core 34 improves blood volumetric and linear flow rates of blood (as compared to closed core designs). This minimizes cardiopulmonary stress associated with reduced volumetric and linear blood flow rates in the central vasculature. Improving blood circulation flow rate optimizes heat transfer between the catheter 10 and the flowing blood.

Should the catheter 10 rest on a portion of a blood vessel wall during operation, the interstices 28 facilitate blood flow to inhibit formation of coagula at the site of contact between the balloon 20 and the vessel wall.

Figure 6:
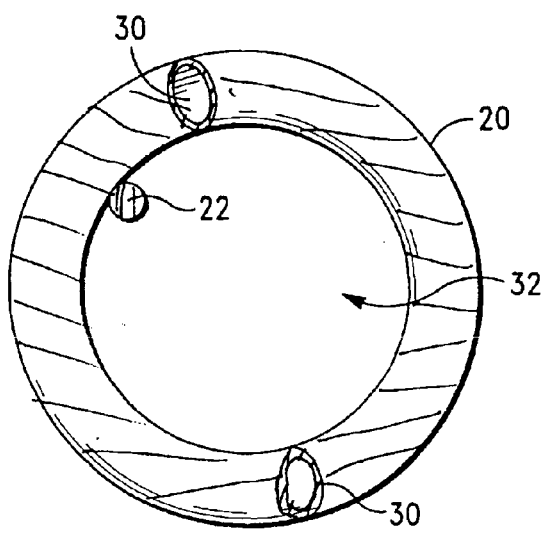
FIG. 6 shows a cross sectional view of the catheter of FIG. 4 as seen along the line 6—6.

FIG. 6 shows balloon 20 fully inflated. Inflation of the balloon 20 causes the heat exchange lumens 30 to achieve a generally round cross section. The heat exchange lumens 30 are shaped to optimize the flow of heat exchange fluid through the heat exchange lumens. The heat exchange lumens 30 form a closed circuit with the heat exchange fluid source 12 (FIG. 1).

Figure 7:
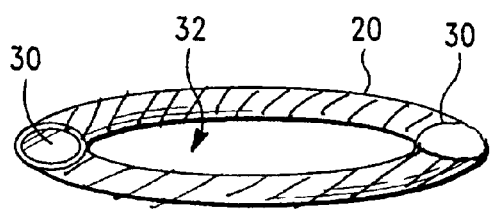
FIG. 7 shows the catheter of FIG. 6 flattened.

FIG. 7 shows the balloon 20 in a collapsed configuration. The heat exchange lumens 30 collapses. Collapsing of heat exchange lumens 30 causes the open core 32 to collapse, either partially or fully. Accordingly, the balloon 20 achieves a collapsed configuration having thin profile that facilitates insertion and removal of the balloon 20 from the vasculature of a patient.

Figure 8:
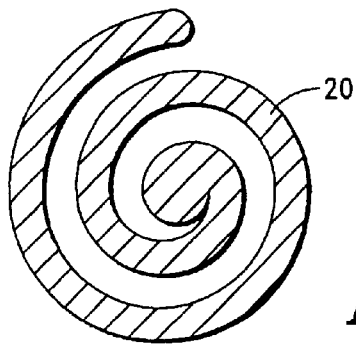
FIG. 8 shows the catheter of FIG. 6 flattened and rolled.

FIG. 8 shows the balloon 20 in a collapsed configuration. The balloon 20 is rolled upon itself to minimize the cross-sectional profile of the balloon 20. A thin cross-sectional profile facilitates insertion of the catheter into the vasculature of a patient through a narrow diameter opening. The thin profile also facilitates removal of the catheter body from the vasculature of the patient. Having a catheter that can achieve a thin profile minimizes patient trauma that is associated with inserting and removing a catheter from the central vasculature.

Figure 9:
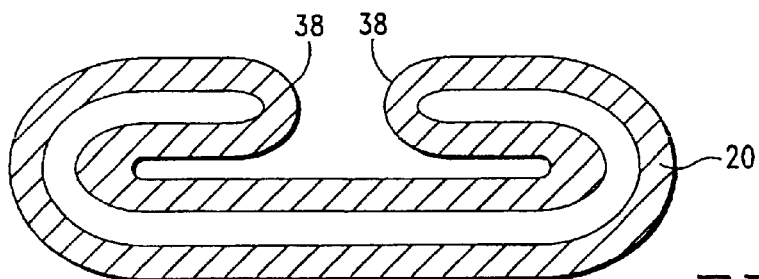
FIG. 9 shows the catheter of FIG. 6 flattened and folded.

FIG. 9 shows the balloon 20 in a collapsed configuration. The balloon 20 has two edges 38. The edges 30 are folded to enable the balloon 20 to fold upon itself and thereby minimize the cross-sectional profile of the balloon 20.

Figure 10:
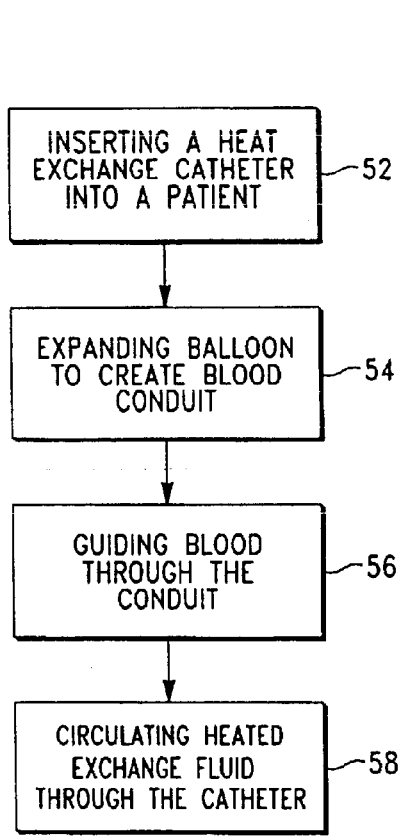
FIG. 10 shows a method of guiding blood through a open core formed by the catheter.

FIG. 10 shows a method of exchanging heat with flowing blood, generally designated with the reference numeral 50. The method 50 includes the inserting 52 a heat exchange catheter into a patient, expanding 54 the balloon to create a blood flow conduit, guiding 56 blood through the conduit, and circulating 58 heat exchange fluid through the catheter.

The step of inserting 52 includes providing a heat exchange catheter having a balloon with a helically wrapped heat exchange element, and inserting the heat exchange catheter into the vasculature of a patient. Preferably the step of inserting 52 includes using a shape memory rod to improve pushability of the catheter and to regulate the shape of the catheter.

The step of expanding 54 includes filling the balloon with heat exchange fluid to inflate the balloon and to define an open core with the balloon. The heat exchange fluid source regulates pressure within the balloon so that the open core continually defines the blood flow conduit.

The open core is centrally aligned within the catheter. The step guiding 56 blood flow through the open core includes guiding blood centrally within the catheter and guiding blood along the outside of the catheter.

According to one aspect of the invention, the step of guiding 56 includes mixing blood from the open core with blood from the outside of the catheter. The helically wrapped heat exchanger has non-contiguous helical winds and defines interstices between the non-contagious helical winds. The step of guiding 56 includes guiding blood through the interstices to mix blood on the outside of the balloon with blood flowing within the open core.

The step of circulating 58 includes circulating heat exchange fluid through a heat exchange fluid source and through the heat exchange element in a closed circuit to exchange heat with the flowing blood.

The foregoing describes examples of various aspects of the present invention. However, it can be appreciated that the configuration and shape of the open core an the heat exchange lumens can be changed to various other shapes to facilitate heat exchange. Further, the number of heat exchange lumens shown can be increased. Accordingly, the present invention should be limited only by the claims below.

What is claimed is:

1. A heat exchange catheter having an open core, comprising:
   a catheter body for use in the central vasculature of a patient, the catheter body having a balloon with at least one heat exchange lumen for exchanging heat with flowing blood;
   the balloon being inflatable from a collapsed configuration to an inflated configuration; and
   the inflated configuration facilitates the flow of heat exchange fluid through the heat exchange lumen, the hear exchange lumen wraps in a helical pattern to define an open core and to enable blood to flow through the open core during use of the catheter, wherein the balloon has a distal end, and an insertion rod attaches to the distal end.

2. A heat exchange catheter as set forth in claim 1, wherein the open core defines an inside and an outside, the heat exchange lumen has contiguous helical winds to isolate the inside from the outside.

3. A heat exchange catheter as set forth in claim 1, wherein the open core defines an inside and an outside, the heat exchange lumen has non-contiguous helical winds to facilitate movement of flowing blood between the inside of the open core and the outside the open core.

4. A heat exchange catheter as set forth in claim 1, further comprising a heat exchange fluid source in communication with the heat exchange lumen, the heat exchange fluid source is pressure regulated for selectively inflating and collapsing the heat exchange lumen.

5. A heat exchange catheter as set forth in claim 1, wherein the catheter body includes an insertion rod for inserting the balloon into a patient when the balloon is in the collapsed configuration.

6. A heat exchange catheter as set forth in claim 1, wherein the rod is fabricated from a shape memory material that biases the balloon into the helical shape under desired conditions, and the rod cooperates with the heat exchange fluid to inflate the balloon.

7. A heat exchange catheter system having a heat exchange catheter with an internal conduit to facilitate blood flow, comprising:
   a heat exchange fluid source having heat exchange fluid;
   a temperature control unit for regulating temperature of a heat exchange fluid;
   a catheter body for use in the central vasculature of a patient, the catheter body having a balloon with at least one heat exchange lumen in fluid communication with the heat exchange fluid source for exchanging heat with flowing blood;
   the balloon being inflatable from a collapsed configuration to an inflated configuration, in the inflated configuration the balloon facilitates the flow of heat exchange fluid through the heat exchange lumen, the heat exchange lumen wraps in a helical configuration to define an open core and to enable blood to flow through the open core during use of the catheter; and
   in the collapsed configuration, the heat exchange lumen collapses and the open core collapses to facilitate insertion and removal of the catheter body into the central vasculature of a patient, wherein the balloon includes an insertion rod and a distal end, the rod attaches to the distal end for inserting the balloon into a patient.

8. A system as set forth in claim 7, wherein the heat exchange fluid source includes a pressure regulator for adjusting pressure in the heat exchange lumen.

9. A heat exchange catheter as set forth in claim 7, wherein the rod is fabricated from a shape memory material so that the rod biases the balloon into the helical shape under desired conditions and cooperates with the heat exchange fluid to inflate the balloon into the inflated configuration.

10. A heat exchange catheter as set forth in claim 7, wherein the open core defines an inside and an outside, the heat exchange lumen has contiguous helical winds to isolate the inside from the outside.

11. A heat exchange catheter as set forth in claim 7, wherein the open core defines an inside and an outside, the heat exchange lumen has non-contiguous helical winds to allow flowing blood to mix between the inside of the open core and the outside the open core.

12. A method of exchanging heat with flowing blood, comprising;
   inserting a heat exchange catheter having a balloon with a helically wrapped heat exchange element into the vasculature of a patient, the step of inserting including using a rod;
   inflating the balloon to define an open core;
   guiding blood flow through the open core; and
   circulating heat exchange fluid through the heat exchange element to exchange heat with the flowing blood.

13. A method as set forth in claim 12, further comprising regulating pressure within the balloon.

14. A method as set forth in claim 13, wherein the step of guiding blood flow includes guiding blood flow outside of the balloon.

15. A method as set forth in claim 14, wherein the helically wrapped heat exchanger has non-contiguous helical winds and defines interstices between the non-contagious helical winds, the step of guiding includes guiding blood through the interstices to mix blood on the outside of the balloon with blood flowing within the open core.

16. A method as set forth in claim 15, wherein the helically wrapped heat exchanger has contiguous helical winds and the open core has an inside and an outside, the method further comprises isolating the inside from the outside.

17. A method as set forth in claim 12, wherein the step of inserting includes shaping the catheter with the rod.

* * * * *